US012601732B2

(12) United States Patent (10) Patent No.: US 12,601,732 B2
Yamamoto et al. (45) Date of Patent: Apr. 14, 2026

(54) CELL IMAGE ANALYSIS DEVICE

(71) Applicant: SHIMADZU CORPORATION, Kyoto (JP)

(72) Inventors: Shuhei Yamamoto, Kyoto (JP); Ryuji Sawada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 483 days.

(21) Appl. No.: 17/919,422

(22) PCT Filed: Feb. 3, 2021

(86) PCT No.: PCT/JP2021/003946
§ 371 (c)(1),
(2) Date: Oct. 17, 2022

(87) PCT Pub. No.: WO2021/215069
PCT Pub. Date: Oct. 28, 2021

(65) Prior Publication Data
US 2023/0160874 A1 May 25, 2023

(30) Foreign Application Priority Data
Apr. 21, 2020 (JP) ................................. 2020-075277

(51) Int. Cl.
*G01N 33/483* (2006.01)
*C12M 1/34* (2006.01)
(Continued)

(52) U.S. Cl.
CPC ......... *G01N 33/4833* (2013.01); *C12M 41/36* (2013.01); *G06T 7/0014* (2013.01);
(Continued)

(58) Field of Classification Search
None
See application file for complete search history.

(56) References Cited

U.S. PATENT DOCUMENTS 11,537,506 B1 * 12/2022 Dasgupta ................. G06N 3/10
2013/0183707 A1 * 7/2013 Mangoubi ............. G16B 40/20
702/19
(Continued)

FOREIGN PATENT DOCUMENTS

CN 109800048 A 5/2019
CN 109816623 A 5/2019
(Continued)

OTHER PUBLICATIONS

Written Opinion for PCT/JP2021/003946 dated Apr. 6, 2021.
(Continued)

*Primary Examiner* — Chan S Park
*Assistant Examiner* — Promotto Tajrian Islam
(74) *Attorney, Agent, or Firm* — Sughrue Mion, PLLC

(57) ABSTRACT

A cell image analysis device includes: a display unit; a storage unit which stores learning data which is a set of data of a cell image and data of an analyzed image in which a region of interest included in the cell image is specified, and a discriminator which is created using a learning model constructed by machine learning using the learning data; a test data input receiver to receive an input of test data; a discriminator evaluation unit to evaluate the discriminator using the test data; an evaluation result storing unit to store evaluation data including the evaluation result of the discriminator and the test data used for the evaluation in association with the discriminator; and a display processor to display the test data and/or the evaluation result associated with the discriminator on a screen of the display unit in response to an input for selecting the discriminator.

13 Claims, 3 Drawing Sheets

| CULTURE CONDITION | accuracy | precision | recall | IoU |
|---|---|---|---|---|
| MSC_P5_CiMS_1e4 | 0.972817 | 0.821963 | 0.772273 | 0.661604 |

(51) Int. Cl.

| | |
|---|---|
| *G06T 7/00* | (2017.01) |
| *G06T 7/155* | (2017.01) |
| *G06V 10/25* | (2022.01) |
| *G06V 10/77* | (2022.01) |
| *G06V 10/774* | (2022.01) |
| *G06V 20/69* | (2022.01) |

(52) U.S. Cl.
CPC .............. *G06T 7/155* (2017.01); *G06V 10/25* (2022.01); *G06V 10/7715* (2022.01); *G06V 10/774* (2022.01); *G06V 20/695* (2022.01)

(56) References Cited

U.S. PATENT DOCUMENTS

| | | | |
|---|---|---|---|
| 2015/0205345 A1* | 7/2015 | Naess ................... | G06F 3/0304 345/156 |
| 2018/0157976 A1* | 6/2018 | Sun ........................ | G06N 3/082 |
| 2019/0156476 A1 | 5/2019 | Yoshida et al. | |
| 2019/0156481 A1 | 5/2019 | Sekiguchi et al. | |
| 2019/0189278 A1 | 6/2019 | Matsumoto et al. | |
| 2019/0355113 A1 | 11/2019 | Wirch et al. | |
| 2021/0019499 A1* | 1/2021 | Takahashi ................. | G06T 5/60 |
| 2021/0019580 A1* | 1/2021 | Sakane ............. | G06V 30/1916 |
| 2021/0103632 A1* | 4/2021 | Kadia ................. | G06F 18/2431 |
| 2021/0224992 A1 | 7/2021 | Mizukami et al. | |
| 2022/0327707 A1* | 10/2022 | Nishide ................. | G16H 50/70 |

FOREIGN PATENT DOCUMENTS

| | | | | | |
|---|---|---|---|---|---|
| JP | 2011229410 A | * | 11/2011 | ........... | C12M 41/14 |
| JP | 2019-109553 A | | 7/2019 | | |
| JP | 2019-211468 A | | 12/2019 | | |
| WO | 2019/117065 A1 | | 6/2019 | | |

OTHER PUBLICATIONS

Jonathan Long, et al., "Fully Convolutional Networks for Semantic Segmentation", The IEEE Conference on Computer Vision and Pattern Recognition (CVPR), 2015, pp. 3431-3440.

Olaf Ronneberger, et al., "U-Net: Convolutional Networks for Biomedical Image Segmentation", Computer Vision and Pattern Recognition (cs.CV) arXiv:1505.04597 [cs.CV].

Japanese Office Action dated Jul. 25, 2023 in Japanese Application No. 2022-516851.

Extended European Search Report dated Sep. 27, 2023 in Application No. 21791950.5.

Communication issued Jun. 13, 2025 in Chinese Application No. 202180039977.2.

Chinese Office Action dated Nov. 18, 2025 in Application No. 202180039977.2.

* cited by examiner

Fig. 2

REGION WHERE CELL IS
ACTUALLY PRESENT

REGION WHERE CELL IS
ESTIMATED TO BE PRESENT

PHASE IMAGE

ANALYZED IMAGE
(CORRECT IMAGE)

ANALYSIS RESULT (DEVIATION
FROM CORRECT IMAGE)

| CULTURE CONDITION | accuarcy | precision | recall | IoU |
|---|---|---|---|---|
| MSC_P5_CiMS_1e4 | 0.972817 | 0.821963 | 0.772273 | 0.661604 |

CELL IMAGE ANALYSIS DEVICE

CROSS REFERENCE TO RELATED APPLICATIONS

This application is a National Stage of International Application No. PCT/JP2021/003946 filed Feb. 3, 2021, claiming priority based on Japanese Patent Application No. 2020-075277 filed Apr. 21, 2020.

TECHNICAL FIELD

The present invention relates to a device for analyzing a cell image.

BACKGROUND ART

In the field of regenerative medicine, in recent years, studies using pluripotent stem cells such as iPS cells, ES cells and mesenchymal stem cells have been conducted. In research and development of regenerative medicine using such pluripotent stem cells, it is necessary to culture a large number of cells. When a large amount of cells to be used for regenerative medicine is cultured, the cells in culture should be observed at an appropriate time point, and the state (for example, whether the proliferation rate of the cells is changed, whether there is a morphological change, whether the undifferentiated state is maintained, or whether bacterial contamination or the like occurs) is examined. In this case, since the observed cells are further cultured after the observation, it is necessary to examine the state of the cells nondestructively and noninvasively. Non-destructive and non-invasive observation of the state of the cells is often performed using an image of the cells.

Since cells are normally thin and transparent, and absorb little light, it is difficult to distinguish a cell from the culture medium in a cell image obtained by light microscopy. Therefore, a phase contrast microscope is widely used for observing cells. In the phase contrast microscope, since the amount of change in phase when light passes through an object is made into an image, even for thin and transparent cells, the cells can be distinguished from the culture medium, and a cell-visible image (phase image) can be obtained.

Non Patent Literature 1 proposes that "the region of a cell nucleus" or "the region occupied by one cell" included in a phase image is extracted as a region of interest using image processing software, and a change in the number of cells or change in cell morphology is analyzed from the region of interest. Various algorithms for removing noise or background are usually provided for such image processing software, and a user can select an appropriate one from these algorithms to remove noise or background. Then, the intensity of each pixel is binarized to determine the position of the cell, and the number and shape of the cells are analyzed.

The shape of a cell varies depending on the type of the cell and the number of days of culture. In addition, the state of the background of the phase image (for example, variation in luminance) varies depending on the type of culture medium. Thus, in order to determine which algorithm is suitable for processing of the phase image to be analyzed, a skill relating to the algorithm of image analysis is required.

Thus, in recent years, it has been proposed to analyze a phase image using a discriminator created by machine learning (for example, Non Patent Literatures 2 and 3). In the analysis of the phase image using the machine learning, a plurality of sets of a phase image of a cell and an analyzed image in which the region of interest of the phase image is specified (for example, "an image obtained by staining a specific protein in a cell in a phase image" or "a region of cells in a phase image determined and designated by an observer as having an abnormal cell morphology") are prepared in advance as learning data and verification data. Then, a learning model is constructed by the machine learning using the learning data. Thereafter, parameters of the learning model are adjusted using the verification data. The learning model thus created is provided as a discriminator for analyzing an actual phase image. By using the discriminator thus provided, a user can analyze the cell image regardless of the skill of the user.

CITATION LIST

Non Patent Literature

Non Patent Literature 1: Kota Miura and Yuki Tsukada, "Starting biological image analysis with ImageJ", Gakken Medical Shujunsha Co., Ltd., April 2016, ISBN: 9784780909364

Non Patent Literature 2: Fully Convolutional Networks for Semantic Segmentation. The IEEE Conference on Computer Vision and Pattern Recognition (CVPR), 2015, pp. 3431-3440

Non Patent Literature 3: U-Net: Convolutional Networks for Biomedical Image Segmentation. Computer Vision and Pattern Recognition (cs.CV) arXiv:1505.04597 [cs.CV]

SUMMARY OF INVENTION

Technical Problem

Accuracy of the analysis of the phase image depends on whether the original learning model of the discriminator used for the analysis has learned phase images having characteristics close to an actual phase image to be analyzed. However, in general, a learning model by machine learning is normally constructed by a software engineer, and a discriminator using such a learning model is incorporated in analysis software in advance and provided to a user. Thus, there is a problem that the user cannot check by himself/ herself whether the discriminator is appropriate or not with respect to the image to be analyzed.

A problem to be solved by the present invention is to provide a cell image analysis device in which a user can check whether a discriminator is appropriate or not with respect to an image to be analyzed by himself/herself.

Solution to Problem

A cell image analysis device according to the present invention made to solve the above problems includes:

a display unit;

a storage unit which stores learning data which is a set of data of a cell image and data of an analyzed image in which a region of interest included in the cell image is specified, and a discriminator which is created using a learning model constructed by machine learning using the learning data, and which outputs data of an image in which the region of interest included in the cell image is estimated according to an input of the data of the cell image;

a test data input receiver configured to receive an input of test data which is a set of data of a cell image different from the learning data and data of an analyzed image of the cell image;

a discriminator evaluation unit configured to evaluate the discriminator by comparing data of an image output from the discriminator with respect to an input of data of the cell image of the test data with data of the analyzed image of the test data;

an evaluation result storing unit configured to store evaluation data including the evaluation result by the discriminator evaluation unit and the test data used for the evaluation in the storage unit in association with the discriminator; and a display processor configured to display the test data and/or the evaluation result associated with the discriminator on a screen of the display unit in response to an input for selecting the discriminator stored in the storage unit.

Advantageous Effects of Invention

The cell image analysis device according to the present invention includes the display unit and the storage unit. The storage unit stores learning data which is a set of data of a cell image and data of an analyzed image in which a region of interest included in the cell image is specified. In addition, the storage unit also stores a discriminator which is created using a learning model constructed by machine learning using the learning data and outputs data of an image in which the region of interest included in the cell image is estimated according to an input of the data of the cell image. One or more discriminators may be stored in the storage unit. When a plurality of the discriminators are stored, each discriminator is associated with the learning data used for machine learning the learning model constituting the discriminator.

In the cell image analysis device according to the present invention, when a user inputs test data which is a set of data of cell image different from the learning data and data of an analyzed image of the cell image, the discriminator is evaluated using the test data and stored together with the test data. Thereafter, the user performs an input for selecting a discriminator to display the test data associated with the discriminator on the screen of the display unit. For example, from similarity between the test data displayed on the screen and the cell image (real cell image) to be actually analyzed, the user can determine whether the discriminator is appropriate or not with respect to analysis of the real cell image. In addition, it is also possible to display the evaluation result performed by inputting the test data by the user himself/ herself on the screen of the display unit and to determine whether the analysis of the real cell image using the discriminator is appropriate or not.

BRIEF DESCRIPTION OF DRAWINGS

FIG. 2 is a screen example when a cell image is imported in the cell image observation system of the present embodiment.

DESCRIPTION OF EMBODIMENTS

Figure 1:
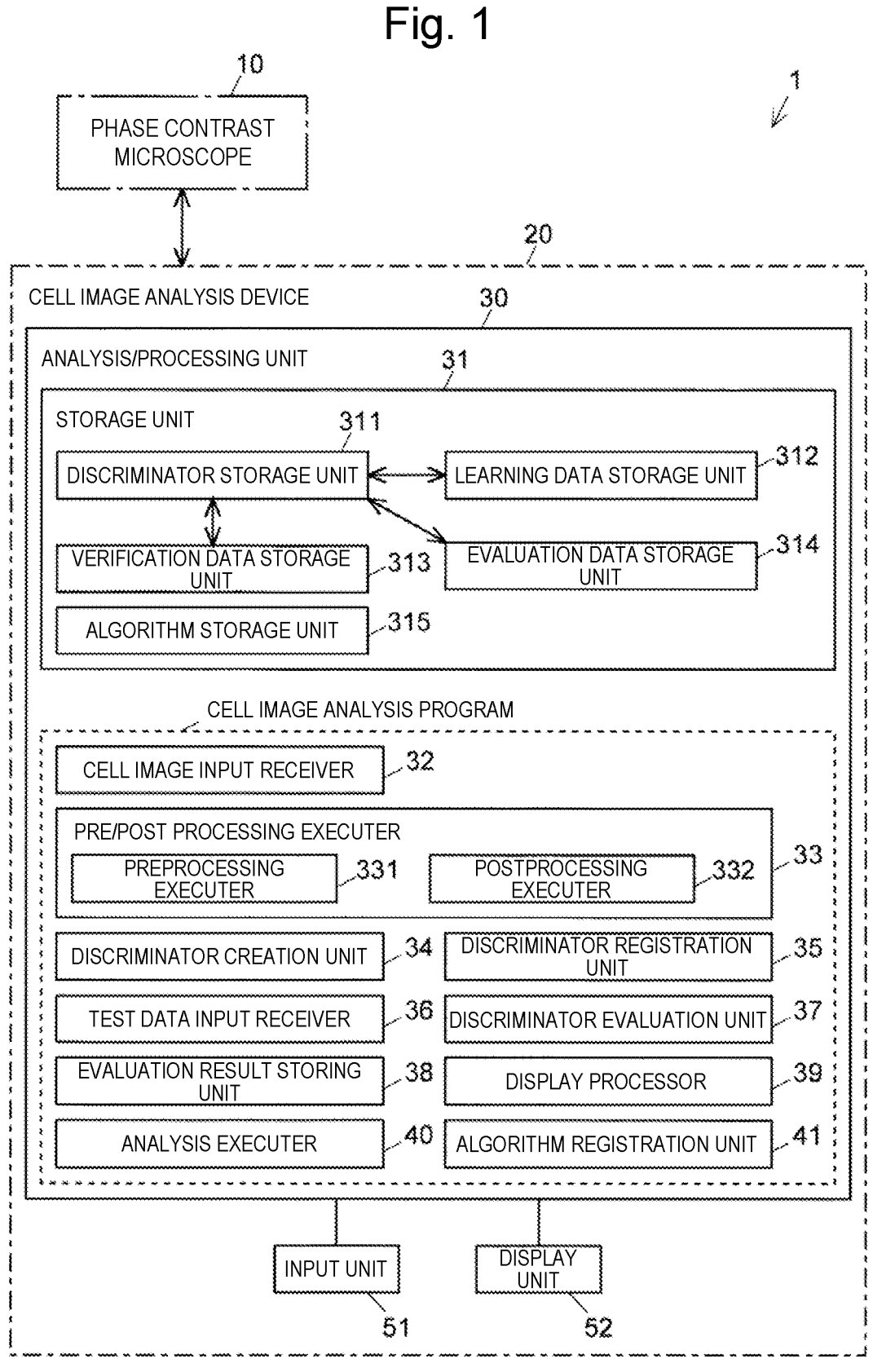
FIG. 1 is a configuration diagram of a main part of a cell image observation system in which an embodiment of a cell image observation device according to the present invention and a microscopic observation unit are combined.

One embodiment of a cell image analysis device according to the present invention will be described below with reference to the drawings. FIG. 1 is a configuration diagram of a main part of a cell image analysis system 1 including a cell image analysis device 20 of the present embodiment.

The cell image analysis system 1 of the present embodiment is roughly composed of a microscopic observation unit 10 and the cell image analysis device 20. The microscopic observation unit 10 of the present embodiment is a phase contrast microscope and can acquire a phase image of cells in a culture plate.

The cell image analysis device 20 includes an analysis/ processing unit 30, and an input unit 51 and a display unit 52 which are connected to the analysis/processing unit 30. In addition to the storage unit 31, the analysis/processing unit 30 includes a cell image input receiver 32, a pre/post processing executer 33, a discriminator creation unit 34, a discriminator registration unit 35, a test data input receiver 36, a discriminator evaluation unit 37, an evaluation result storing unit 38, a display processor 39, an analysis executer 40, and an algorithm registration unit 41 as functional blocks. The pre/post processing executer 33 includes a preprocessing executer 331 and a postprocessing executer 332. The analysis/processing unit 30 is constituted of a personal computer and a workstation, and the above-described functional blocks are embodied by executing a cell image analysis program installed in advance.

The storage unit 31 is provided with a discriminator storage unit 311. The discriminator storage unit 311 stores a plurality of different discriminators depending on the type of the cell to be analyzed and the analysis content. The type of the cell is, for example, an iPS cell, an ES cell, or a cancer cell. The analysis contents are, for example, determination of the number of cells, determination of cell coverage, and determination of the number of differentiated cells.

The storage unit 31 is provided with a learning data storage unit 312, a verification data storage unit 313, an evaluation data storage unit 314, and an algorithm storage unit 315. The learning data storage unit 312 stores a large number of pieces of learning data which is a set of phase image data of a cell and data of an analyzed image (for example, an image obtained by staining a specific intracellular protein which is a region of interest included in the cell image) of the phase image. The learning data is associated with culture information (type of cell, culture condition, type of staining substance at time of creating analyzed image, and the like). The culture conditions include the type of culture medium and the number of culture days.

The verification data storage unit 313 stores a set of phase image data of a cell and analyzed image data of the phase image different from the learning data. The evaluation data storage unit 314 stores test data which is a set of phase image data of a cell and analyzed image data of the phase image different from the learning data and the verification data and data of an evaluation result of the discriminator using the test data. The verification data and the test data are also associated with the culture information.

The algorithm storage unit 315 stores information related to an algorithm (preprocessing algorithm) related to preprocessing of the phase image and a stained image, and a postprocessing algorithm (postprocessing algorithm) used after specification of the region of interest by the discriminator. Different preprocessing algorithms are stored for each cell type and culture condition.

The preprocessing algorithm is used, for example, for positioning between the phase image and the stained image, noise removal from the phase image and the stained image, background removal from the phase image and the stained image, and binarization processing of the stained image. For example, a linear filter, a median filter, and the like can be used to remove noise. For example, an average value filter and the like can be used to remove background.

As the postprocessing algorithm, different postprocessing algorithms are stored according to contents of analysis (for example, calculation of a morphological feature value of the region of interest estimated by the discriminator, evaluation of correlation of the morphological feature value, graphing of a temporal change of the morphological feature value, graphing of the morphological feature value with respect to the culture condition, and calculation of a ratio between the region of interest and a background region). The morphological feature value of the region of interest is, for example, the number, area, roundness, aspect ratio, and perimeter of the region of interest, lengths of a long side and a short side of a rectangle circumscribing the region of interest, and a centroid position.

Next, procedures of various operations using the cell image analysis system 1 of the present embodiment will be described.

A procedure in which a user constructs a learning model and creates a discriminator will be described. In advance, the user collectively saves, in one folder, a file describing image information of cells and data of observation images of cells (for example, the phase image acquired by a phase contrast microscope and the stained image acquired by an optical microscope after performing a staining process after acquiring the phase image). The image information includes a project name, a name of a person in charge, a plate name, and a well type in addition to the culture information.

When the user makes an input instructing creation of the discriminator, the discriminator creation unit 34 operates each functional block as follows.

First, the cell image input receiver 32 causes the display unit 52 to display a screen which allows the user to designate a place where data to be used for constructing the learning model is stored. When the user designates a storage location of image data or the like, the cell image input receiver 32 reads image information and image data stored in the storage location, and displays an image on the screen of the display unit 52.

Figure 2:
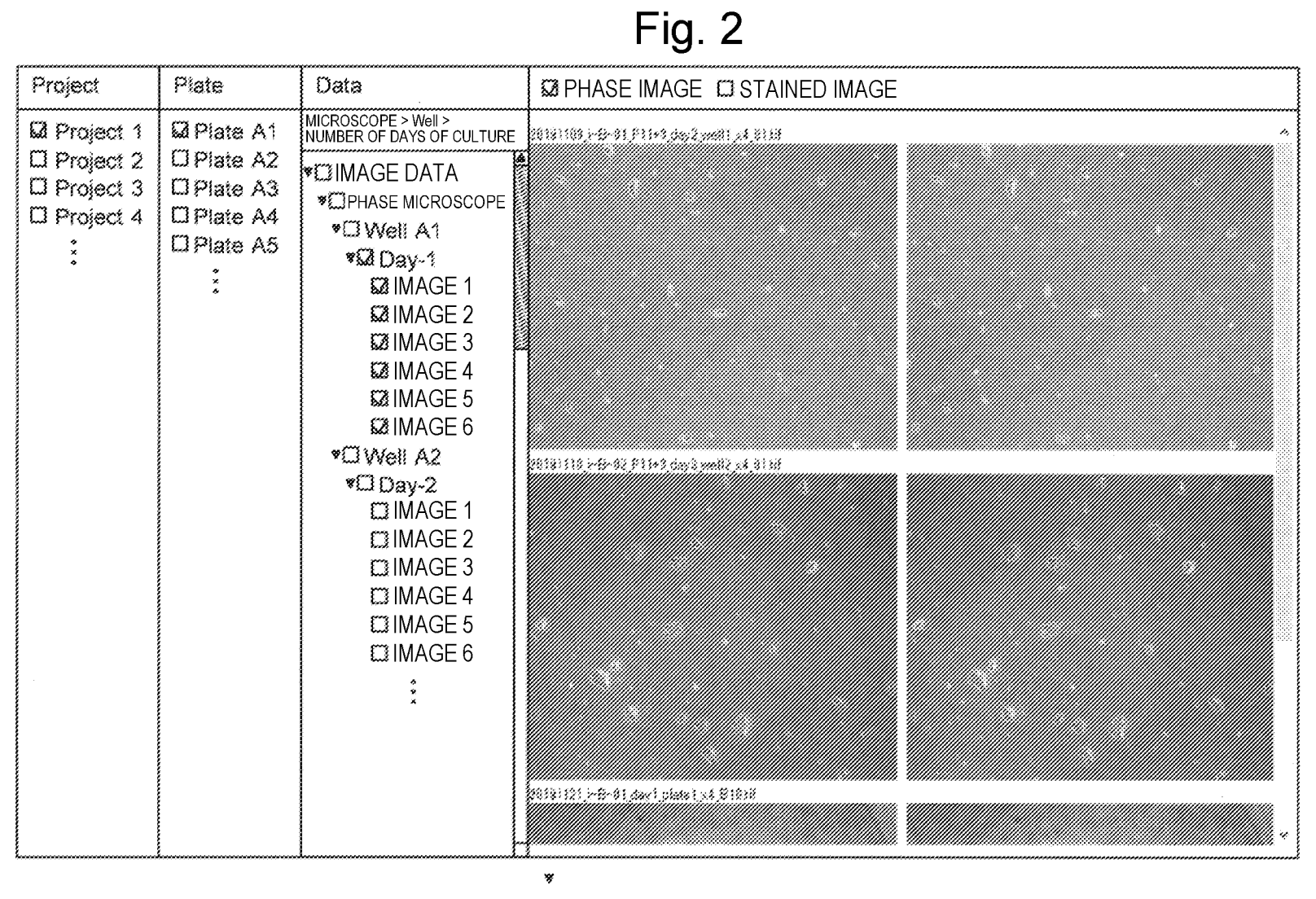

FIG. 2 is a display example of the screen, and a project selection field, a plate selection field, a data selection field, and an image display field are provided in order from the left side. In this example, when a project and a plate are selected, data acquired by the selected project and plate is displayed in a tree view. When the user checks a check box displayed together with the name of the image data, the corresponding image is displayed in the image display field. The user confirms the image displayed in the image display field and determines an image to be used for creating the discriminator. In FIG. 2, the phase image is displayed in the image display field; however, the display of the phase image and the stained image can be switched.

When the user determines data to be used for constructing the learning model from the displayed phase image (or stained image), the preprocessing executer 331 reads out the preprocessing algorithm corresponding to the culture condition included in the image condition of the image data determined by the user from the algorithm storage unit 315.

The preprocessing executer 331 first detects positions of a plurality of reference points included in the phase image and the stained image, and positions the phase image and the stained image based on the positions. When the phase image and the stained image have different magnification ratios, the magnification ratios of the phase image and the stained image are matched. Subsequently, noise and background are removed from the phase image and the stained image using the read-out preprocessing algorithm. In addition, luminance of each pixel is binarized based on the luminance value of each pixel in the stained image and a binarization reference value set in advance in the preprocessing algorithm. Hereinafter, the preprocessed stained image (binarized image) is also referred to as an analyzed image.

When the preprocessing of the phase image and the stained image is completed, the cell image input receiver 32 displays a data sorting setting screen on the display unit 52. The data sorting setting screen is used to set a ratio at which a set of pieces of image data to be imported is sorted to the learning data, the verification data, and the test data, and a ratio of learning data:verification data:test data=6:3:1 is set as an initial value. Although the user can appropriately change this ratio, even in this case, it is preferable to allocate at least 10% as the test data.

When the user performs a predetermined operation such as pressing a determination button, a plurality of sets of pieces of image data selected by the user are sorted into the learning data, the verification data, and the test data at the above ratio, and the respective pieces of data are stored in the learning data storage unit 312, the verification data storage unit 313, and the evaluation data storage unit 314. When the user changes the ratio, the sets of pieces of image data are sorted according to the changed ratio, and are stored in the learning data storage unit 312, the verification data storage unit 313, and the evaluation data storage unit 314. Depending on the number of sets of pieces of image data, the image data may not be sorted according to the above ratio. In this case, the set of pieces of image data may be preferentially sorted in the order of the test data, the learning data, and the verification data. For example, when the number of sets of pieces of image data is 48, 5 sets (4.8 which is $\frac{1}{10}$ of 48 is rounded up) may be allocated as the test data, 29 sets (28.7 which is $\frac{2}{3}$ of 43 which is the number of sets after sorting into the test data is rounded up) may be allocated as the learning data, and 14 sets (remaining number) may be allocated as the verification data.

When the sets of pieces of image data are sorted, it is preferable to randomly sort the number of sets of pieces of image data corresponding to the ratio. This is because, for example, when the sets of pieces of image data are sorted in the order of the file names by the number corresponding to the ratio, there is a case where a deviation occurs in the characteristics of the image data sorted as the learning data. For example, there is a possibility that only data with a short (or long) culture day (a set of pieces of image data with biased culture conditions) is allocated as the learning data. In this case, a discriminator is created by the learning model in which the phase image with a long (or short) culture day is not learned, and there is a possibility that the cell with a long (or short) culture day cannot be correctly distinguished.

Next, the discriminator creation unit 34 reads out an unlearned machine learning model stored in advance in the storage unit 31. As the machine learning model, for example, a model which performs deep learning can be used. Alternatively, a plurality of types of machine learning models including a support vector machine (SVM), a random forest, and the like may be prepared, and the user may select the machine learning model to be used for creating the discriminator from among the machine learning models.

The discriminator creation unit 34 causes the unlearned learning model to execute machine learning in which the data of the phase image of the learning data is used as input data and the analyzed image is used as correct output data. In addition, a parameter value of the learning model is adjusted using the verification data. Then, a discriminator is created from the created learning model, and evaluation is performed using the test data.

For example, in the case of the discriminator which estimates the region of interest from the phase image, what are called Accuracy, Precision, Recall, and IoU (Intersection over Union) are known as indices of evaluation. As conceptually shown in FIG. 3, when a region where the cell is actually present and is estimated to be present is a region A, a region where the cell is actually present but is not estimated to be present is a region B, a region where the cell is not actually present but is estimated to be present is a region C, and a region where the cell is not actually present and is estimated to be not present is a region D, these indices are obtained by the following calculation formulas. Which index is used for evaluation of the discriminator may be determined in advance, or may be selected by the user each time.

Accuracy=A+D/total area
Precision=A/A+C
Recall=A/A+B
IoC=A/A+B+C

The machine learning using the learning data and the adjustment of the parameter value using the verification data are repeated until the index value reaches a predetermined reference value in the evaluation using the test data. When the index value reaches the predetermined reference value in the evaluation using the test data, the discriminator creation unit 34 creates a discriminator from the learning model and stores the discriminator in the discriminator storage unit 311. In addition, the learning data and the verification data used for constructing the learning model, and the test data and the evaluation result used for the evaluation are associated with the discriminator. The discriminator thus created is then used to analyze the actual cell image.

In the cell image analysis system 1 of the present embodiment, not only the discriminator is newly created, but also the discriminator stored in the discriminator storage unit 311 can be improved. In that case, instead of reading out the unlearned learning model, the user may select the discriminator stored in the discriminator storage unit 311, and then cause the learning model constituting the discriminator to perform machine learning in the same procedure as described above. As a result of verification by the inventor, for example, it has been found that the discriminator can be applied to analysis of mesenchymal stem cells (non-colony cells) by improving the discriminator created based on image data of iPS cells (colony cells).

In addition, in the cell image analysis system 1 of the present embodiment, the discriminator can be imported from another cell image analysis device, or the discriminator can be exported for use in another cell image analysis device.

When the user instructs the export of the discriminator, the discriminator registration unit 35 displays, on the display unit 52, a screen which allows the user to designate the discriminator to be exported and a place of an export destination (save destination). When the user designates the discriminator to be exported and the save destination, the discriminator registration unit 35 reads out the learning data, the verification data, the test data, and the evaluation result associated with the discriminator (that is, having been used for the preparation and evaluation of the discriminator) from the learning data storage unit 312, the verification data storage unit 313, and the evaluation data storage unit 314, respectively. Then, a data file of the discriminator, files of the learning data, the verification data, and the test data, and a data file of the evaluation result are output to the designated storage location.

When the user instructs the import of the discriminator, the discriminator registration unit 35 displays, on the display unit 52, a screen for allowing the user to designate the storage location of the data to be imported. When the user designates the storage destination, the discriminator registration unit 35 reads the data file of the discriminator, the files of the learning data, the verification data, and the test data, and the data file of the evaluation result from the storage destination. Then, the data file of the discriminator is stored in the discriminator storage unit 311, the file of the learning data is stored in the learning data storage unit 312, the file of the verification data is stored in the verification data storage unit 313, and the file of the test data and the data file of the evaluation result are stored in the evaluation data storage unit 314.

When the user creates or improves the discriminator by himself/herself as described above, the actual cell image may be analyzed using the discriminator. However, when the actual cell image is analyzed using the discriminator stored in advance, it is necessary to check which discriminator stored in the discriminator storage unit 311 is suitable for the analysis.

In the cell image analysis system 1 of the present embodiment, the user can check the learning data and the verification data used for constructing the learning model used for creating the discriminator, the test data, and the evaluation result for each discriminator stored in the discriminator storage unit 311. In addition, the phase image (phase image in which the type of cell, the type of culture medium, and the like are the same or approximate) having characteristics similar to those of the cell image which is about to be analyzed and the analyzed image of the phase image can be used as the test data to evaluate the discriminator. The procedure of such work will be described below.

When the user performs an input operation of selecting one of the discriminators stored in the discriminator storage unit 311, the display processor 39 reads out the learning data associated with the selected discriminator from the learning data storage unit 312, reads out the verification data from the verification data storage unit 313, reads out the test data and the evaluation result from the evaluation data storage unit 314, and displays the data on the screen of the display unit 52. The user can check similarity between the displayed learning data and verification data and the characteristics of the phase image to be actually analyzed and examine whether the discriminator is appropriate or not. In addition, reliability of the evaluation result for the analysis of the phase image to be performed can be confirmed based on the similarity between the displayed test data and the characteristics of the phase image to be actually analyzed.

When the user performs an input operation for instructing execution of evaluation of the discriminator selected from the discriminator storage unit 311, the discriminator evaluation unit 37 operates each functional block as follows.

First, the test data input receiver 36 displays a screen prompting an input of the test data on the display unit 52. The test data is a data set including a plurality of sets of the phase image and the analyzed image. The test data can be input in the same procedure as the above-described input of the learning data and the like. That is, the phase image and the stained image are stored in the same folder together with the culture information of the cell in advance, and first, the folder is designated to cause the test data input receiver 36 to read these pieces of information. Then, the preprocessing executer 331 performs preprocessing such as removing noise from the phase image and the stained image to create test data. Naturally, a set of the phase image and the analyzed image already subjected to such preprocessing may be input.

When the test data is input (or created), the discriminator evaluation unit 37 sequentially inputs the phase images included in the test data to the discriminator selected by the user. Then, the image (image in which the region of interest is estimated) output from the discriminator is compared with the analyzed image of the test data and evaluated. Accuracy, Precision, Recall, and IoU described above can be used as indices of this evaluation.

Figures 3, 4:
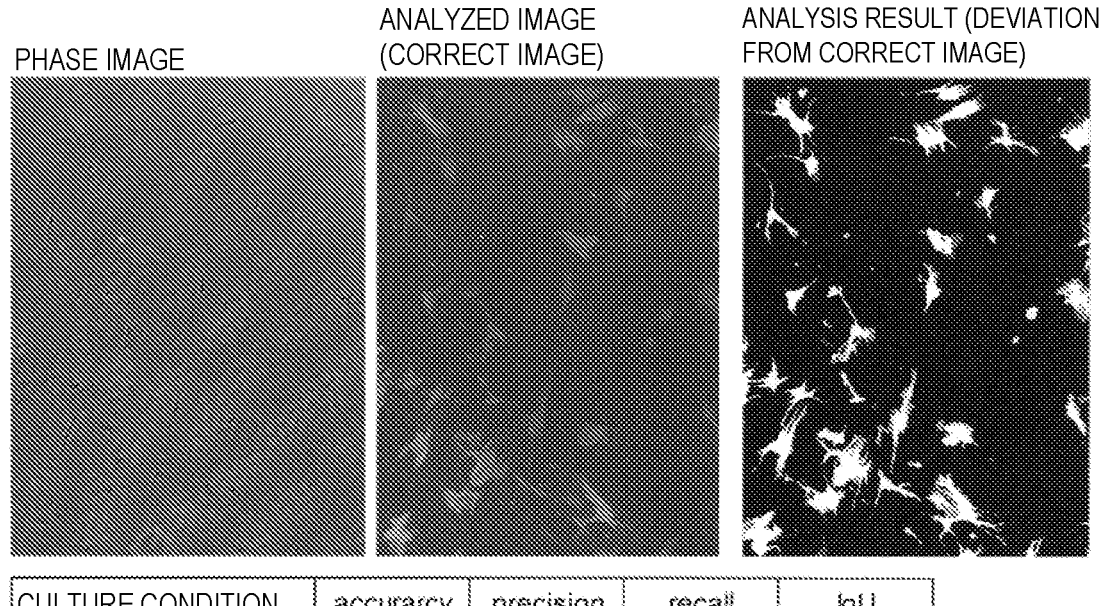
FIG. 3 is an explanatory view related to an index of evaluation of a discriminator in the cell image observation system of the present embodiment.
FIG. 4 is a display example of an evaluation result of the discriminator in the cell image observation system of the present embodiment.

When the evaluation of the discriminator by the discriminator evaluation unit 37 is completed, the evaluation result storing unit 38 stores evaluation data including the evaluation result of the discriminator and the test data used for the evaluation in the evaluation data storage unit 314 in association with the discriminator. The display processor 39 displays the result on the screen of the display unit 52. FIG. 4 shows a display example relating to the evaluation result of the discriminator. In this display example, on the screen indicating the evaluation result of the discriminator, the phase image, the analyzed image (correct image which is the stained image after the preprocessing), an image (analysis result) indicating a deviation between the image of the estimation result by the discriminator and the correct image, and the evaluation value are displayed. Although FIG. 4 is shown in monochrome, a colored image is actually displayed to improve visibility.

For example, a region where the cell is correctly estimated can be displayed in white (corresponding to the region A in FIG. 3), a region where background is correctly estimated can be displayed in black (corresponding to the region D in FIG. 3), a region where the cell is actually present but is not estimated to be present can be displayed in red (corresponding to the region B in FIG. 3), and a region where the cell is actually not present but is estimated to be present can be displayed in green (corresponding to the region C in FIG. 3). Although FIG. 4 is a display example of a result of evaluating the discriminator using a set of the phase image and the stained image as the test data, the discriminator can also be evaluated using a plurality of sets of the phase image and the stained image as the test data. In this case, each of the plurality of sets of pieces of image data is displayed in the same manner as in FIG. 4, and the evaluation value for each image data and the evaluation value (for example, an average of the evaluation value for each image data) related to the entire plurality of sets of pieces of image data are displayed.

As described above, in the cell image analysis device of the present embodiment, the user can evaluate the discriminator by himself/herself using the phase image and the stained image which the user has.

Next, a procedure in which the user executes analysis of the cell image to be actually analyzed will be described.

The user sets the culture plate containing the cell to be analyzed at a predetermined position of the microscopic observation unit 10, and performs a predetermined operation by the input unit 51. As a result, the microscopic observation unit 10 photographs a sample (cells in the culture plate) to generate phase image data. The user performs the same processing on all the culture plates on which the cells to be analyzed are cultured to acquire the phase image data, and stores the phase image data in a predetermined folder. In this example, the case where the phase image is acquired using the microscopic observation unit 10 has been described; however, the phase image data acquired in advance may be stored in a predetermined folder. The user also saves a file describing image information including the culture information of the cell to be analyzed in the same folder as the phase image data.

Thereafter, when the user designates the folder and instructs execution of analysis of the phase image of the cell, the analysis executer 40 operates each functional block as follows.

First, the cell image input receiver 32 reads out the phase image data and the culture information included in the image information from the designated folder. Subsequently, the analysis executer 40 displays a screen for allowing the user to designate the analysis content. The analysis contents may include, for example, determination of the number of cells, determination of cell coverage, and determination of the number of differentiated cells. When the user designates the analysis content, the analysis processor reads out the discriminator corresponding to the read-out culture information and analysis content from the discriminator storage unit 311. In addition, the preprocessing algorithm and the postprocessing algorithm corresponding to the read-out culture information are read out from the algorithm storage unit 315. The analysis executer 40 displays the read-out discriminator, preprocessing algorithm, and postprocessing algorithm on the screen of the display unit 52.

When the user checks the displayed discriminator, preprocessing algorithm, and postprocessing algorithm and performs a predetermined operation such as pressing a determination button, a sequence of image analysis processing is determined. When the plurality of discriminators, preprocessing algorithms, and postprocessing algorithms corresponding to the culture information and the analysis content are stored, all of them are displayed on the screen of the display unit 52. In this case, the user is allowed to designate one preprocessing algorithm and one or a plurality of combinations of the discriminators and the postprocessing algorithms. For example, when both the number of cells and the cell coverage are analyzed, the user may designate the set of the discriminator and the postprocessing algorithm corresponding to each analysis. When the user designates a plurality of sets of the discriminator and the postprocessing algorithm, an analysis sequence for continuously executing the plurality of processings is determined.

When the analysis sequence is determined, the preprocessing executer 331 collectively performs preprocessing based on the preprocessing algorithm on all the imported phase images. Next, the analysis executer 40 inputs the data of the preprocessed phase image to the discriminator, and outputs the data of the image in which the region of interest is specified. For example, when the analysis content is determination of the number of cells, data of an image in which a nucleus of the cell included in the phase image is specified is output, and when the analysis content is determination of the cell coverage, data of an image in which the entire cytoskeletal region of each cell is specified is output.

When the image data is output from the discriminator, the postprocessing executer 332 executes analysis using the postprocessing algorithm. For example, when the analysis content is determination of the number of cells, the number of nuclei of cells included in the image data output from the discriminator is obtained and output as an analysis result. When the analysis content is determination of the cell coverage, a ratio of the cytoskeletal region to the entire region of the image data output from the discriminator is obtained and output as an analysis result.

In the above description, the case where the discriminator, the preprocessing algorithm, and the postprocessing algorithm corresponding to the culture condition for the cell to be analyzed are stored in the discriminator storage unit 311 and the algorithm storage unit 315, respectively, has been described as an example. However, when an image of a cell cultured using a new type of cell or culture medium is analyzed, there is a case where the discriminator, the preprocessing algorithm, and the postprocessing algorithm corresponding to the culture information are not stored. In addition, when analysis of contents which has not been performed conventionally is executed, there is a case where the corresponding discriminator or postprocessing algorithm is not stored.

Since the creation and import of a new discriminator can be performed in the same procedure as the processing by the discriminator creation unit 34 and the discriminator registration unit 35 described above, the description will be omitted. Hereinafter, a procedure for adding a new preprocessing algorithm and/or a new postprocessing algorithm will be described.

When the user performs an input operation for instructing addition of the algorithm, the algorithm registration unit 41 prompts the user to designate which of the preprocessing algorithm and the postprocessing algorithm is to be registered. When the user designates addition of the preprocessing algorithm, the user is further prompted to input the culture information of the cell using the preprocessing algorithm, and is prompted to designate the storage location of the preprocessing algorithm. When the user inputs the culture information of the cell and designates the storage location of the preprocessing algorithm, the file in which the preprocessing algorithm is described is imported from the storage location and stored in the algorithm storage unit 315 in association with the culture condition.

When the user designates addition of the postprocessing algorithm, the user is further prompted to input the culture information of the cell using the postprocessing algorithm and the content of the analysis performed by the algorithm, and is prompted to designate the storage location of the postprocessing algorithm. When the user inputs the culture information and the analysis content of the cell and designates the storage location of the postprocessing algorithm, the file in which the postprocessing algorithm is described is imported from the storage location and stored in the algorithm storage unit 315 in association with the culture condition.

As described above, in the cell image analysis system 1 of the present embodiment, even in the case where the image of the cell cultured using a new type of cell or culture medium is analyzed, or in the case where analysis of contents which has not been performed conventionally is executed, the preprocessing algorithm, the postprocessing algorithm, and the discriminator corresponding to the case can be appropriately added.

In the cell image analysis system 1 of the above embodiment, the discriminator can be created and improved using the data of the cell image and the data of the stained image possessed by the user. Thus, it is not necessary to provide the cell image to an external software engineer in order to create the discriminator, and thus, it is possible to maintain confidentiality regarding the cell image and the analysis of the cell image.

In the cell image analysis system 1 of the above embodiment, the cell image analysis device 20 can be configured as a cloud server, and can be configured to be accessible from a plurality of research bases. By adopting such a configuration, it is possible to utilize a large number of discriminators corresponding to cell images obtained at the plurality of research bases, analyzed data of the images, and various types of cells, culture conditions, and analysis contents as a recorded database.

The above-described embodiment is merely an example, and can be appropriately modified in accordance with the spirit of the invention. In the above embodiment, the case where the cultured cells are observed with the phase microscope to acquire and analyze the phase image has been described. However, the same configuration as in the above embodiment can also be used for analysis of images observed with other types of microscopes.

In the cell image analysis device of the above embodiment, a plurality of discriminators corresponding to the same culture information and analysis content may be stored in the discriminator storage unit 311. In that case, for example, it is preferable to store a simple discriminator which can specify the region of interest in a short time although discrimination accuracy is not so high, and a high-accuracy discriminator which takes time to specify the region of interest but has high discrimination accuracy. As a result, for example, it is possible to achieve proper use of the discriminator, such as use of the simple discriminator in a case where an operation of narrowing down the phase image of the cultured cells by screening is performed, and use of the high-accuracy discriminator in a case where the phase image after narrowing down is analyzed in detail, and it is possible to enhance analysis efficiency.

Modes

It is understood by those skilled in the art that the plurality of exemplary embodiments described above are specific examples of the following modes.

Clause 1

A cell image analysis device according to one mode including:

a display unit;

a storage unit which stores learning data which is a set of data of a cell image and data of an analyzed image in which a region of interest included in the cell image is specified, and a discriminator which is created using a learning model constructed by machine learning using the learning data and outputs image data in which the region of interest included in the cell image is estimated according to an input of the data of the cell image;

a test data input receiver configured to receive an input of test data which is a set of data of a cell image different from the learning data and data of an analyzed image of the cell image;

a discriminator evaluation unit configured to evaluate the discriminator by comparing data of an image output from the discriminator with respect to an input of data of a cell image of the test data with data of an analyzed image of the test data;

an evaluation result storing unit configured to store evaluation data including an evaluation result by the discriminator evaluation unit and the test data used for the evaluation in the storage unit in association with the discriminator; and a display processor configured to display the test data and/or the evaluation result associated with the discriminator on a screen of the display unit in response to an input for selecting the discriminator stored in the storage unit.

In the cell image analysis device according to Clause 1, when a user inputs test data which is the set of the data of the cell image different from the learning data and the data of the analyzed image of the cell image, the discriminator is evaluated using the test data and stored together with the test data. Thereafter, the user performs an input for selecting the discriminator to display the test data associated with the discriminator and/or the contents of the evaluation by the discriminator evaluation unit on the screen of the display unit. For example, from similarity between the test data displayed on the screen and the cell image (real cell image) to be actually analyzed, the user can determine the discriminator is appropriate or not with respect to analysis of the real cell image. In addition, from the evaluation result of the discriminator using test data similar to a real cell image, it is possible to determine whether the analysis of the real cell image using the discriminator is appropriate or not.

Clause 2

In the cell image analysis device according to Clause 1, a plurality of the discriminators are stored in the storage unit, and learning data used to create the discriminator is associated with each of the discriminators.

In the cell image analysis device according to Clause 2, an appropriate discriminator can be selected from a plurality of discriminators according to an image to be analyzed and a purpose of analysis.

Clause 3

In the cell image analysis device according to Clause 1 or Clause 2, different discriminators are stored in the storage unit according to a type of cell and/or a culture condition.

In the cell image analysis device according to Clause 3, the cell image can be analyzed using a discriminator suitable for the type of cell and/or the culture condition.

Clause 4

In the cell image analysis device according to any one of Clause 1 to Clause 3,
    the display processor is configured to display, as the evaluation result, a cell image and an analyzed image of the test data, and an image indicating a deviation between the analyzed image and an image output from the discriminator.

In the cell image analysis device according to Clause 4, the evaluation result of the discriminator can be visually checked.

Clause 5

The cell image analysis device according to any one of Clause 1 to Clause 4, further including
    a cell image input receiver configured to receive an input of a plurality of sets of data of the cell image and data of the analyzed image in which the region of interest included in the cell image is specified, and information on the culture condition regarding the plurality of sets of data of images, and store the input in the storage unit in association with each other.

In the cell image analysis device according to Clause 5, the set of the data of the cell image possessed by the user and the data of the analyzed image can be managed in association with the information on the culture condition of the cell.

Clause 6

The cell image analysis device according to Clause 5, further including
    a discriminator creation unit configured to create a discriminator by constructing a learning model by machine learning using the plurality of sets of data of images received by the cell image input receiver.

In the cell image analysis device according to Clause 6, the user can create the discriminator by himself/herself.

Clause 7

In the cell image analysis device according to Clause 6,
    the cell image input receiver is configured to create learning data and verification data by sorting the plurality of sets of data of images received by the cell image input receiver at a predetermined ratio, and
    the discriminator creation unit is configured to construct the learning model by executing the machine learning using the learning data and the verification data sorted by the cell image input receiver.

In the cell image analysis device according to Clause 7, since the learning data and the verification data are automatically created from the set of the data of the cell image and the data of the analyzed image, the discriminator can be easily created.

Clause 8

The cell image analysis device according to any one of Clause 5 to Clause 7, further including
    a discriminator registration unit configured to receive an input of the discriminator stored in the storage unit, a set of the data of the cell image associated with the discriminator and data of the analyzed image of the cell image, and the culture condition, and store the input in the storage unit.

In the cell image analysis device according to Clause 8, a discriminator created by another cell image analysis device can be imported together with the set of the data of the cell image corresponding to the discriminator and the data of the analyzed image of the cell image, and the culture condition.

Clause 9

The cell image analysis device according to any one of Clause 5 to Clause 8, further including
    a discriminator output unit configured to output the discriminator stored in the storage unit together with the set of the data of the cell image associated with the discriminator and the data of the analyzed image of the cell image, and the culture condition.

In the cell image analysis device according to Clause 9, the discriminator created by the device can be exported to another cell image analysis device together with the set of the data of the cell image corresponding to the discriminator and the data of the analyzed image of the cell image, and the culture condition.

Clause 10

The cell image analysis device according to any one of Clause 1 to Clause 9, further including:

a preprocessing algorithm storage unit which stores a preprocessing algorithm for preprocessing the data of the cell image and the data of the analyzed image; and a preprocessing executer configured to perform preprocessing of the data of the cell image and the data of the analyzed image using the preprocessing algorithm stored in the preprocessing algorithm storage unit.

Clause 11

In the cell image analysis device according to Clause 10, the preprocessing executer is configured to execute at least one of positioning, noise removal, and background removal of the data of the cell image and the data of the analyzed image, and binarization of luminance of the data of the analyzed image.

In the cell image analysis device according to Clause 10 and Clause 11, the data of the cell image and the data of the analyzed image can be easily preprocessed.

Clause 12

The cell image analysis device according to any one of Clause 1 to Clause 11, further including:

a postprocessing algorithm storage unit which stores a postprocessing algorithm for postprocessing the data of the image output from the discriminator; and a postprocessing executer configured to perform postprocessing of the data of the image output from the discriminator using the postprocessing algorithm stored in the postprocessing algorithm storage unit.

Clause 13

In the cell image analysis device according to Clause 12, the postprocessing executer is configured to execute at least one of calculation of a morphological feature value (the number, area, roundness, aspect ratio, and perimeter of the region of interest, lengths of a long side and a short side of a rectangle circumscribing the region of interest, and a centroid position) of the region of interest estimated, evaluation of correlation of the morphological feature value, graphing of a temporal change of the morphological feature value, graphing of the morphological feature value with respect to the culture condition, and calculation of a ratio between the region of interest and a background region in the data of the image output from the discriminator.

In the cell image analysis device according to Clause 12 and Clause 13, the data of the image output from the discriminator can be easily preprocessed.

REFERENCE SIGNS LIST

1 . . . Cell Image Analysis System
10 . . . Microscopic Observation Unit
20 . . . Cell Image Analysis Device
30 . . . Analysis/Processing Unit
31 . . . Storage Unit
311 . . . Discriminator Storage Unit
312 . . . Learning Data Storage Unit
313 . . . Verification Data Storage Unit
314 . . . Evaluation Data Storage Unit
315 . . . Algorithm Storage Unit 32 . . . Cell Image Input Receiver
33 . . . Pre/Post Processing Executer
331 . . . Preprocessing Executer
332 . . . Postprocessing Executer
34 . . . Discriminator Creation Unit
35 . . . Discriminator Registration Unit
36 . . . Test Data Input Receiver
37 . . . Discriminator Evaluation Unit
38 . . . Evaluation Result Storing Unit
39 . . . Display Processor
40 . . . Analysis Executer
41 . . . Algorithm Registration Unit
51 . . . Input Unit
52 . . . Display Unit

The invention claimed is:

1. A cell image analysis method comprising:

a preparation step of preparing a discriminator which is created using a learning model constructed by machine learning using learning data, and which outputs data of an analyzed assessment image in which a region of interest included in an assessment cell image is estimated according to an input of data of the assessment cell image, the learning data being at least one set of data of a learning cell image and data of a learning analyzed image in which a region of interest included in the learning cell image is specified;

a test data input reception step of receiving an input of test data which is a set of data of a test cell image and data of a test analyzed image of the test cell image different from the learning data, the test cell image including a cell image in which a type of cell or a type of culture medium is/are same or approximate with those of the assessment a cell image;

a discriminator evaluation step of evaluating the discriminator by comparing data of a test image output from the discriminator with respect to an input of data of the test cell image of the test data with the data of the test analyzed image of the test data, and obtaining an evaluation result;

a selection step of selecting the discriminator based on the evaluation result; and an analysis step of inputting data of the assessment cell image to the discriminator selected, and obtaining an output related to data of the analyzed assessment image in which the region of interest included in the assessment cell image is estimated.

2. The cell image analysis method according to claim 1, wherein a plurality of the discriminators are prepared in the preparation step, and the learning data used to create the discriminator is associated with each of the discriminators.

3. The cell image analysis method according to claim 1, wherein different discriminators are prepared in the preparation step according to the type of cell and/or a the type of culture condition.

4. The cell image analysis method according to claim 1, wherein the learning data comprises a plurality of sets of data of the learning cell image and data of the learning analyzed image in which the region of interest included in the learning cell image is specified further comprising a cell image input reception step receiving an input of the plurality of sets of data of the learning cell image and data of the learning analyzed image in which the region of interest included in the learning cell image is specified, and an input of information regarding a respective a culture condition associated with the plurality of sets of data of the learning cell images.

5. The cell image analysis method according to claim 4, further comprising a discriminator creation step of creating the discriminator by constructing the learning model by machine learning using the plurality of sets of data of the learning cell image and learning analyzed image received in the cell image input reception step.

6. The cell image analysis method according to claim 5, wherein further creating learning data and verification data by sorting the plurality of sets of data of the learning cell images received in the cell image input reception step at a predetermined ratio, and further constructing the learning model in the discriminator creation step by executing the machine learning using the learning data and the verification data sorted in the cell image input reception step.

7. The cell image analysis method according to claim 1, further comprising: an algorithm preparing step of preparing a preprocessing algorithm for preprocessing the data of the learning cell image and the data of the analyzed learning image; and a preprocessing step of performing preprocessing of the data of the learning cell image and the data of the learning analyzed image using the preprocessing algorithm prepared in the algorithm preparing step.

8. The cell image analysis method according to claim 7, wherein at least one of positioning, noise removal, or background removal of the data of the learning cell image and the data of the analyzed learning image, and binarization of luminance of the data of the analyzed learning image is executed in the preprocessing step.

9. The cell image analysis method according to claim 1, further comprising:

an algorithm preparing step of preparing a postprocessing algorithm for postprocessing the data of the analyzed assessment image output from the discriminator; and a postprocessing step of performing postprocessing of the data of the analyzed assessment image output from the discriminator using the postprocessing algorithm prepared in the algorithm preparing step.

10. The cell image analysis method according to claim 9, wherein at least one of calculation of a morphological feature value of the region of interest estimated, graphing of a temporal change of the morphological feature value, graphing of the morphological feature value with respect to the culture condition, or calculation of a ratio between the region of interest and a background region in the data of the analyzed assessment image output from the discriminator is executed in the postprocessing step.

11. A cell image analysis device comprising:

a display unit;

a storage unit which stores learning data which is a plurality of sets of data of a learning cell image and data of a learning analyzed image in which a region of interest included in the learning cell image is specified, and a discriminator which is created using a learning model constructed by machine learning using the learning data, and which outputs data of an analyzed assessment image in which the region of interest included in an assessment cell image is estimated according to an input of the data of the assessment cell image;

a test data input receiver configured to receive an input of test data which is a set of data of a test cell image and data of a test analyzed image of the test cell image different from the learning data;

a discriminator evaluation unit configured to evaluate the discriminator by comparing data of a test image output from the discriminator with respect to an input of data of the test cell image of the test data with the data of the test analyzed image of the test data;

an evaluation result storing unit configured to store evaluation data including an evaluation result by the discriminator evaluation unit and the test data used for the evaluation in the storage unit in association with the discriminator;

a display processor configured to display the evaluation result associated with the discriminator on a screen of the display unit in response to an input for selecting the discriminator stored in the storage unit;

a cell image input receiver configured to receive an input of the plurality of sets of data of the learning cell image and data of the learning analyzed image in which the region of interest included in the learning cell image is specified, and an input of information on the culture condition regarding the plurality of sets of data of the learning cell images, and store the input in the storage unit in association with each other; and a discriminator registration unit configured to receive an input of the discriminator stored in the storage unit, a set of the data of the learning cell image and data of the learning analyzed image of the learning cell image associated with the discriminator, and the culture condition, and store the input in the storage unit.

12. A cell image analysis device comprising:

a display unit;

a storage unit which stores learning data which is a plurality of sets of data of a learning cell image and data of a learning analyzed image in which a region of interest included in the learning cell image is specified, and a discriminator which is created using a learning model constructed by machine learning using the learning data, and which outputs data of an analyzed assessment image in which the region of interest included in an assessment cell image is estimated according to an input of the data of the assessment cell image;

a test data input receiver configured to receive an input of test data which is a set of data of a test cell image and data of a test analyzed image of the test cell image different from the learning data;

a discriminator evaluation unit configured to evaluate the discriminator by comparing data of a test image output from the discriminator with respect to an input of data of the test cell image of the test data with the data of the test analyzed image of the test data, and obtaining an evaluation result;

an evaluation result storing unit configured to store evaluation data including the evaluation result by the discriminator evaluation unit and the test data used for the evaluation in the storage unit in association with the discriminator;

a display processor configured to display the evaluation result associated with the discriminator on a screen of the display unit in response to an input for selecting the discriminator stored in the storage unit;

a cell image input receiver configured to receive an input of the plurality of sets of data of the learning cell image and data of the learning analyzed image in which the region of interest included in the learning cell image is specified, and an input of information on the culture condition regarding the plurality of sets of data of the learning cell images, and store the input in the storage unit in association with each other; and a discriminator output unit configured to output the discriminator stored in the storage unit together with the set of the data of the learning cell image and the data of the analyzed learning image of the learning cell image associated with the discriminator, and the culture condition.

13. A cell image analysis device comprising:

a display unit;

a storage unit which stores learning data which is a set of data of a learning cell image and data of a learning analyzed image in which a region of interest included in the learning cell image is specified, and a discriminator which is created using a learning model constructed by machine learning using the learning data, and which outputs data of an analyzed assessment image in which the region of interest included in an assessment cell image is estimated according to an input of the data of the assessment cell image;

a test data input receiver configured to receive an input of test data which is a set of data of a test cell image and data of a test analyzed image of the test cell image different from the learning data, the test cell image including a cell image in which a type of cell or a type of culture medium is/are same or approximate with those of the assessment cell image;

a discriminator evaluation unit configured to evaluate the discriminator by comparing data of a test image output from the discriminator with respect to an input of data of the test cell image of the test data with the data of the test analyzed image of the test data; and obtaining an evaluation result;

an evaluation result storing unit configured to store evaluation data including the evaluation result by the discriminator evaluation unit and the test data used for the evaluation in the storage unit in association with the discriminator; and a display processor configured to display the evaluation result associated with the discriminator on a screen of the display unit in response to an input for selecting the discriminator stored in the storage unit.

* * * * *